United States Patent [19]

Cross

[11] 3,979,409

[45] Sept. 7, 1976

[54] NOVEL PROCESS FOR THE PREPARATION OF 3,5-DIPHENYL-4-PYRAZOLOL AND CERTAIN DERIVATIVES THEREOF

[75] Inventor: Barrington Cross, Rocky Hill, N.J.

[73] Assignee: American Cyanamid Company, Stamford, Conn.

[22] Filed: Oct. 20, 1975

[21] Appl. No.: 624,156

[52] U.S. Cl. .......................... 260/310 R; 260/310 A
[51] Int. Cl.$^2$ ...................................... C07D 231/18
[58] Field of Search .................... 260/310 R, 310 A

[56] References Cited
OTHER PUBLICATIONS

Bull. Soc. Chim. Belg. vol. 61, pp. 331–351 (1952).

Ledrut et al., Compt, Rend. vol. 231, pp. 1513–1515 (1950).

Chemical Abstracts vol. 11:2780$^5$ (1917); vol. 49:15863h (1955); vol. 54:6698i, 6699f and 1285h (1960).

*Primary Examiner*—Donald B. Moyer
*Attorney, Agent, or Firm*—Harry H. Kline

[57] ABSTRACT

There is provided a method for the preparation of 3,5-diphenyl-4-pyrazolol and certain derivatives thereof which are useful as intermediates for the preparation of 4-alkoxy and 4-benzyloxypyrazolium herbicides and fungicides.

7 Claims, No Drawings

NOVEL PROCESS FOR THE PREPARATION OF 3,5-DIPHENYL-4-PYRAZOLOL AND CERTAIN DERIVATIVES THEREOF

BACKGROUND

Application for U.S. Pat., Ser. No. 584,686, filed on June 6, 1975, which is a continuation-in-part of Ser. No. 487,826, filed on July 12, 1974 as well as application for U.S. Pat., Ser. No. 598,527, filed on July 23, 1975, which is a continuation-in-part of Ser. No. 541,900, filed on Jan. 1, 1975 now abandoned, all of which are incorporated herein by reference, describe and claim substituted 4-alkoxy and 4-benzyloxypyrazolium compounds, and methods of use thereof for the control of broadleaf weeds, grass weeds and of plant pathogenic fungi.

The key intermediates for the preparation of the above-identified herbicidal and fungicidal pyrazolium compounds are represented by a 3,5-diphenyl-4-pyrazolol compound of formula:

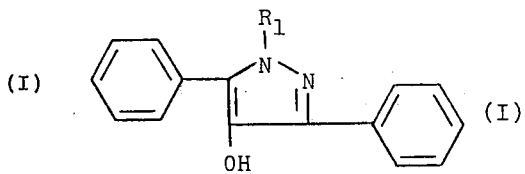

wherein $R_1$ hydrogen or a $C_1$-$C_6$ straight chain or branched alkyl.

Hitherto, formula (I) 4-pyrazolol intermediates have been prepared by various known processes, which though suitable for preparations on a laboratory scale are not satisfactory for the preparation of said compounds in large quantities. These processes, hereinbelow briefly described, utilize relatively expensive starting materials, such as 1,3-diphenyl-1,3-propanedione, or hazardous materials such as p-toluenesulfonylazide. Further, said processes which utilize a plurality of steps yield the desired formula (I) 3,5-diphenyl-4-pyrazolols only in low yields.

Thus M. J. Nye and W. P. Tang [*Tetrahedron*, 28, 1152 (1952)] describe the preparation of a formula (I) pyrazolol wherein $R_1$ is methyl, comprising condensing 2-acetoxy-1,3-diphenyl-1,3-propanedione, with methylhydrazine followed by hydrolysis of the acetyl group, as hereinbelow illustrated:

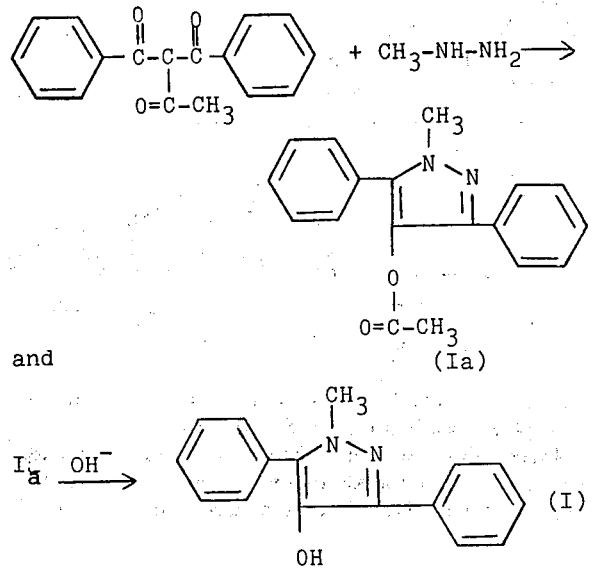

The intermediate 2-acetoxy-1,3-diphenyl-1,3-propanedione itself is prepared from 1,3-diphenyl-1,3-propanedione by bromination to obtain the 2-bromo analog and subsequent replacement of the bromo group with acetoxy. See R. de Neufville and H. V. Pechmann. *Chem. Berichte* 23, 3325 (1890).

Nye and Tang also describe in *Can. J. of Chem.* 48, 3563 (1970) the preparation of 3,5-diphenyl-4-pyrazolol by the following routes:

A. Condensation of 1,3-diphenylpropanetrione (prepared from 1,3-diphenyl-1,3-propanedione) with hydrazine;

B. Condensation of 2-acetoxy-1,3-diphenyl-1,3-propanedione (prepared from 1,3-diphenyl-1,3-propanedione as hereinabove described) with hydrazine followed by alkaline hydrolysis;

C. Condensation of chalcone epoxide with p-toluenesulfonylhydrazide, followed by oxidation with chromium trioxide (20% yield); or D. Condensation of 1,3-diphenyl-2-propanone with p-toluenesulfonylazide in the presence of sodium ethoxide (45% yield).

As hereinabove mentioned, these processes utilize relatively expensive starting materials (A and B) or hazardous materials (C and D) or the products are obtained in low yields (C and D), thus rendering the above processes unattractive.

SUMMARY OF THE INVENTION

The present invention provides a novel process for the preparation of 3,5-diphenyl-4-pyrazolol compounds of formula (I):

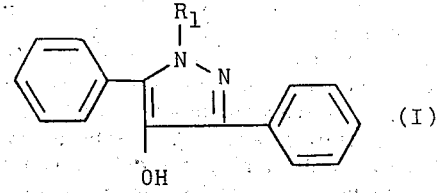

wherein $R_1$ is a member selected from the group consisting of hydrogen and alkyl $C_1$-$C_6$ straight chain or branched; comprising dehydrogenating a 3,5-diphenyl-pyrazol-2-in-4-ol of formula (II) with an equimolar or slight excess amount of N-bromo- or N-chlorosuccinimide in the presence of an anhydrous halogenated hydrocarbon solvent to obtain the desired formula (I) 4-pyrazolols in good yields and purity. The above reaction scheme may be graphically illustrated as follows:

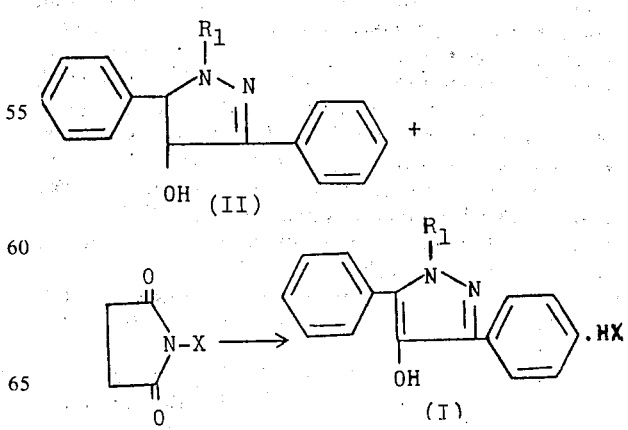

wherein $R_1$ is as defined above and C is bromine or chlorine.

Advantageously, a formula (II) 3,5-diphenylpyrazol-2-in-4-ol wherein $R_1$ is hydrogen is readily prepared by a process described in the application for U.S. Pat.: Ser. No. 379,031, filed July 13, 1973 and allowed Feb. 27, 1975, as follows: 2,3-epoxy-3-phenylpropiophenone is condensed with an equimolar or excess amount of hydrazine to yield the desired 3,5-diphenylpyrazol-2-in-4-ol in excellent yields. Similarly, substitution of a $C_1$-$C_6$ alkylhydrazine for hydrazine in the above reaction affords the corresponding 1-($C_1$-$C_6$) alkyl-3,5-diphenylpyrazol-2-in-4-ols, respectively. The above reaction may be graphically illustrated as follows:

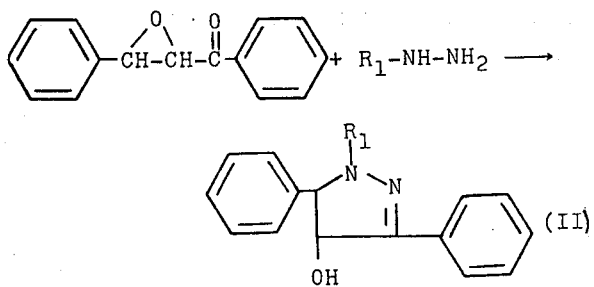

wherein $R_1$ is hydrogen or alkyl $C_1$-$C_6$. Attempts to convert the above formula (II) pyrazolinol to the desired formula (I) pyrazolol by conventional dehydrogenation (oxidation) procedures, e.g: $I_2$/NaHCO$_3$ in methanol, chloranil in methanol, 5% Pd/C in acetonitrile or xylene, MnO$_2$ in benzene, Δ, CCl$_4$, HgO in benzene, KMnO$_4$ in aq. NaOH, CrO$_3$ in pyridine, H$_2$O$_2$ in DMF, Cu(OAc)$_2$ and NaOCl have failed. Sulfur in solvents such as benzene, toluene, xylene, DMF or sulfur alone (in a melt) gave predominantly 3,5-diphenyl-pyrazole and only trace amounts of 3,5-diphenyl-4-pyrazolol. Lead tetraacetate produced up to 38 percent of pyrazolol, but the process was not satisfactory. Thus, reagents customarily employed to dehydrogenate (oxidize) pyrazolines to pyrazoles cannot be utilized to dehydrogenate the pyrazol-2-in-4-ols of formula (II) to the desired formula (I) 4-pyrazolols; the end product most often obtained is the corresponding pyrazole indicating an intramolecular dehydration rather than the desired dehydrogenation.

Surprisingly however, when a formula (II) 3,5-diphenylpyrazol-2-in-4-ol wherein $R_1$ is as defined above is treated with an equimolar or slight excess (10 to 20 percent) amount of N-bromo- or N-chlorosuccinimide in an anhydrous chlorinated hydrocarbon solvent such as chloroform, dichloroethane, trichloroethylene and the like at a temperature range from about 20° to about 100°C, and preferably 20° to 60°C, a rapid reaction takes place with subsequent precipitation of the hydrobromide or hydrochloride of the corresponding formula (I) 3,5-diphenyl-4-pyrazolol in yields of 78 to 84 percent of theory. Treatment of the above salts with aqueous alkali such as sodium or potassium carbonate or acetate affords the corresponding free base, quantitatively.

The novel process of this invention is especially suitable and is preferred for the preparation of 3,5-diphenyl-4-pyrazolol.

Advantageously 3,5-diphenyl-4-pyrazolol may be selectively alkylated or benzylated with alkyl or benzyl halide and base on the oxygen rather than on the ring nitrogen to yield the appropriate 4-alkoxy-3,5-diphenylpyrazole of formula (III), such as 4-benzyloxy-3,5-diphenylpyrazole, in high yields.

To obtain said 4-alkoxy-pyrazoles of formula (III), 3,5-diphenyl-4-pyrazolol is dissolved in a suitable solvent selected from the group consisting of a $C_1$-$C_4$ aliphatic alcohol, acetonitrile, dimethyl formamide, dimethyl sulfoxide and the like or mixtures thereof, but preferentially in methanol, and reacted with an equimolar or slight excess (10 to 20 percent) amount of the appropriate alkyl- or benzyl halide in the presence of an acid acceptor such as sodium carbonate, sodium methoxide or the like, at a temperature range from 50° to 60°C until the reaction is essentially complete. The above reaction may be graphically illustrated as follows:

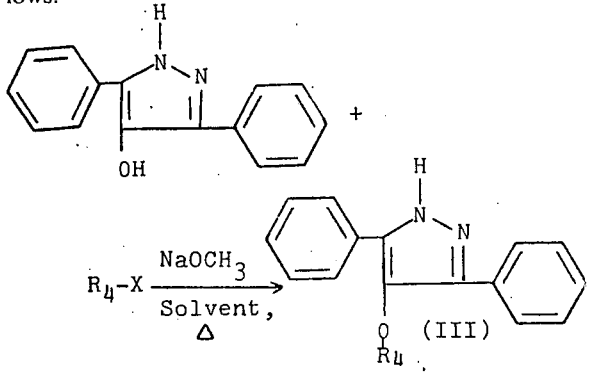

wherein $R_4$ is alkyl $C_1$-$C_4$ straight chain or branched or benzyl; X is bromine or chlorine.

The thus obtained formula III 4-alkoxy- or benzyloxy-3,5-diphenylpyrazoles may then be alkylated or benzylated with equal ease under surprisingly mild conditions to yield 1-alkyl or benzyl)-4-alkoxy or benzyloxy)-3,5-diphenylpyrazoles of formula (IV).

In general, a formula (III) pyrazole wherein $R_4$ is as above defined is dissolved in a $C_1$-$C_3$ alcohol, preferably methanol, and reacted with an equimolar or excess (10 to 50 percent) amount of the appropriate alkylhalide or benzyl halide in the presence of an acid acceptor such as potassium t-butoxide at a temperature range from about 20° to about 50°C, and preferably 20° to 30°C until the reaction is essentially complete. The above reaction may be graphically illustrated as follows:

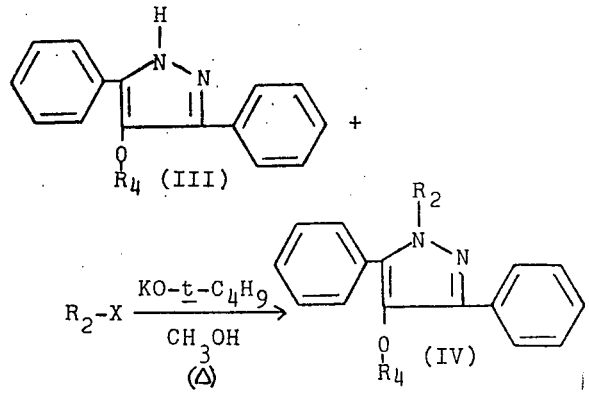

wherein $R_2$ is alkyl $C_1$-$C_6$ straight chain or branched; or benzyl; $R_4$ and X are as defined above.

Preparation of the herbicidal and fungicidal pyrazolium compounds of the hereinabove identified applications for U.S. Patents is accomplished by alkylating a formula IV pyrazole with one or more equivalents of an alkylating agent such as alkyl halides, alkyl sulfates, dialkyl sulfates, alkyl phosphates, alkyl p-toluenesulfonates and the like in a solvent such as benzene, toluene, xylene or the like, generally at a temperature between 50° and 150°C, and preferably, at a temperature between 50° and 130°C.

It is found, that in practice, the thus obtained quaternary compounds are generally most effective as herbicides when applied to the foliage of undesirable plants at rates between about 0.25 and 10 pounds per acre, calculated as the cation.

In utilizing said pyrazolium compounds for protecting plants from pathogenic fungi, it has been found most advantageous to apply the active material to the foliage of the plant in the form of solutions or suspensions containing from about 20 ppm to 5600 ppm of the pyrazolium cation.

The invention is further illustrated by the examples set forth below which are provided by way of illustration and not by way of limitation.

EXAMPLE 1
Preparation of 3,5-Diphenyl-1-methyl-4-pyrazolol

To a suspension of 3,5-diphenyl-1-methylpyrazol-2-in-4-ol (5.0 g, 0.02 mole) in chloroform (50 ml) at room temperature N-bromosuccinimide (3.57 g, 0.02 mole) is added all at once with stirring. After 15 minutes the mixture is heaed to reflux, cooled the solid filtered off and added to 5 percent aqueous sodium acetate. The mixture is stirred for 2 hours, the white solid filtered off to yield 3,5-diphenyl-1-methyl-4-pyrazolol, m.p. 157° to 160°C, in a 36% yield.

Similarly, substitution of 1-ethyl-, 1-propyl- and 1-butyl-3,5-diphenylpyrazol-2-in-4-ol for the corresponding 1-methyl analog in the above reaction yields 1-ethyl-, 1-propyl- and 1-butyl-3,5-diphenyl-4-pyrazolol.

EXAMPLE 2
Preparation of 3,5-Diphenylpyrazol-2-in-4-ol

To a suspension of 2,3-epoxy-3-phenylpropiophenone in 2-propanol, hydrazine hydrate is added at 75°C over a 1½ hour period. The reaction is exothermic. On completion of the addition the reaction mixture is stirred overnight at room temperature. The desired product is obtained in 91% yield.

Similarly, substitution of methyl-, ethyl-, propyl- and butylhydrazine for hydrazine hydrate in the above reaction yields 1-methyl-, 1-ethyl-, 1-propyl- and 1-butyl-3,5-diphenylpyrazol-2-in-4-ol.

EXAMPLE 3
Preparation of 3,5-Diphenyl-4-pyrazolol hydrochloride

Solid N-chlorosuccinimide (2.8 g, 0.021 mole) is added to a stirred suspension of 3,5-diphenylpyrazol-2-in-4-ol (4.7 g, 0.02 mole) in chloroform (200 ml). The reaction mixture is stirred 1 hour at room temperature, refluxed 1 hour, cooled to 40°C and filtered. The solid isolated by filtration is washed with chloroform and dried to yield white crystals (4.5 g, 83% yield), m.p. 262° to 266°C (decomp.).

EXAMPLE 4
Preparation of 3,5-Diphenyl-4-pyrazolol hydrobromide

A slurry of N-bromosuccinimide (39.2 g, 0.22 mole) in hot chloroform (ca. 50 ml) is added over a 40 minute period to a suspension of 3,5-diphenylpyrazol-2-in-4-ol (47.6 g, 0.2 mole) in chloroform (500 ml) at 60°C. The addition causes momentary formation of a brown color. The reaction mixture exotherms and as a result, no heating is required during the addition of the N-bromosuccinimde. After the addition is completed, the reaction mixture of heated at 60°C for ½ hour, filtered hot, the isolated solid washed with chloroform (300 ml) and dried. The solid (50 g, 78.8% yield) is obtained as white crystals, m.p. 299° to 308°C.

EXAMPLE 5
Preparation of 3,5-Diphenyl-4-n-propoxypyrazole

A mixture of 3,5-diphenyl-4-pyrazolol (10.0 g, 0.042 mole), sodium methoxide (2.27 g, 0.042 mole) and methanol (60 ml) is heated at 60°C for 2 hours. Then 1-bromopropane (5.17 g, 0.042 mole) is added slowly (5 minutes) at 60°C. The reaction mixture is then held at 60°C for 7 hours, and slowly cooled to room temperature. Examination by glc at this point indicates that the reaction is incomplete. The mixture is heated to 60°C and more 1-bromopropane (0.26 g, 0.002 mole) added. When the reaction is complete (as shown by glc), the mixture is poured into water and the solid formed is isolated by filtration. The solid (11.5 g, 99.7% yield) m.p. 132° and 136°C contains 2 minor impurities as indicated by tlc (benzene/silica gel). Recrystallization from acetonitrile affords white crystals (7.4 g, 63%) m.p. 142° to 142.5°C.

EXAMPLE 6
Preparation of 4-Benzyloxy-3,5-diphenylpyrazole

A mixture of 3,5-diphenyl-4-pyrazolol (10 g, 0.042 mole), sodium methoxide (2.27 g, 0.042 mole) and methanol (60 ml) is heated at 60°C for 2 hours. Benzyl chloride (5.33 g, 0.042 mole) is then added slowly (10 minutes) at 60°C. A white solid forms. Heating is continued overnight at 60°C. The reaction mixture is then examined by glc and found to be complete. The mixture is poured into water and the solid isolated by filtration. The solid is washed well with water and dried to yield 12.84 g (94%) product.

Recrystallization of a small sample from acetonitrile gives pale yellow crystals, m.p. 152° to 152.5°C.

EXAMPLE 7
General method for the preparation of 1-substituted 4-benzyloxy-3,5-diphenylpyrazoles A mixture of 4-benzyloxy-3,5-diphenylpyrazole (0.0278 mole), potassium t-butoxide (0.0306 mole) and 2-propanol (90 ml) is stirred rapidly at room temperature until a clear solution forms. The appropriate alkyl- or arylalkyl halide (0.0337 mole) is then added dropwise. The reaction mixture is next stirred for 1 to 2 days at room temperature and is then examined by glc or tlc (benzene/silica gel). The reaction mixture is then heated at 50°C for 2 to 4 hours, poured into water and extracted with chloroform or toluene. The organic layer is separated, washed well with water, dried (MgSO$_4$) and stripped under vacuum to afford the product of an oil or as a solid.

The compounds prepared by the above method are listed in Table I below:

Table I

Preparation of 1-Substituted 4-benzyloxy-3,5-diphenylpyrazole

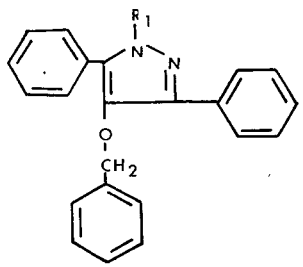

| R₁ | Alkylating Agent | Method of Purification | m.p. °C | Yield % | | Calculated | Found |
|---|---|---|---|---|---|---|---|
| $C_2H_5-$ | $C_2H_5I$ | Chromatographed on Silica gel/$CHCl_3$; recrystallized from 2-propanol | 54.55 | 63.2 | C<br>H<br>N | 81.82<br>6.26<br>7.90 | 81.12<br>6.30<br>7.86 |
| $n-C_3H_7-$ | $n-C_3H_7Br$ | Recrystallized from acetonitrile | 69.70 | 65.6 | C<br>H<br>N | 81.49<br>6.57<br>7.60 | 82.40<br>7.97<br>6.06 |
| $n-C_5H_{11}-$ | $n-C_5H_{11}Br$ | — | oil | 100 | C<br>H<br>N | 81.78<br>7.12<br>7.07 | 81.40<br>7.52<br>6.78 |
| $CH_2=CH-CH_2-$ | $CH_2=CH-CH_2Br$* | Chromatographed on silica gel/toluene | oil | 55.3 | C<br>H<br>N | 79.21<br>6.96<br>8.80 | 78.95<br>6.84<br>8.62 |
| phenyl-$CH_2-$ | phenyl-$CH_2-Cl$ | Recrystallized from 2-propanol | 64.5–68.5 | 48.3 | C<br>H<br>N | 83.63<br>5.81<br>6.73 | 82.93<br>5.85<br>6.80 |

*Exotherm noted during addition

EXAMPLE 8

Preparation of 1-Allyl-3,5-diphenyl-4-n-propoxypyrazole 3,5-Diphenyl-4-n-propoxypyrazole (9.0 g, 0.038 mole) is dissolved in 2-propanol (90 ml). Potassium t-butoxide (4.65 g, 0.042 mole) is added at room temperature and the reaction mixture stirred and heated at 50°C for 3 hours. It is then cooled to room temperature and 3-bromoprop-1-ene (5.53 g, 0.046 mole) is added dropwise. A white solid forms. Stirring is continued at room temperature overnight, the mixture is then poured into water and extracted with chloroform. The chloroform layer is washed with water (3 × 150 ml) and stripped under vacuum. The residual oil is purified by dry column chromatography (silica gel/toluene). The toluene solution is stripped under vacuum to afford 6.64 g (55%) product.

3,5-Diphenyl-1-methyl-4-n-propoxypyrazole is prepared in a similar manner. Yield: 2.76 g (53%), m.p. 62° to 73°C.

EXAMPLE 9

Preparation of 1,2-Dimethyl-3,5-diphenyl-4-n-propoxypyrazolium methyl sulfate 3,5-Diphenyl-1-methyl-4-n-propoxypyrazole (2.77 g, 0.0095 mole) in molecular sieve dried toluene (80 ml) is heated to 50°C and dimethyl sulfate (2.5 g, 0.02 mole) is added. The mixture is stirred and heated under reflux for 6 hours, cooled and set aside overnight. The reaction mixture is then extracted with water, the water layer evaporated to dryness under vacuum to afford the title compound as a hygroscopic solid in 96% yield.

EXAMPLE 10

By the methods of Examples 5, 7 and 9 the following compounds are prepared: 1,2-dimethyl-3,5-diphenyl-4-methoxypyrazolium methyl sulfate; 4-benzyloxy-1,2-dimethyl-3,5-diphenylpyrazolium methyl sulfate; 1-benzyl-3,5-diphenyl-4-methoxy-2-methylpyrazolium methyl sulfate; 1,2-dimethyl-3,5-diphenyl-4-i-propoxypyrazolium methyl sulfate; 3,5-diphenyl-1-ethyl-4-methoxy-2-methylpyrazolium perchlorate; 3,5-diphenyl-4-methoxy-2-methyl-1-n-propylpyrazolium perchlorate, the perchlorate salt being formed by reacting the corresponding methyl sulfate compound with dilute perchloric acid.

EXAMPLE 11

Attempts to dehydrogenate (oxidize) 3,5-diphenyl-1-methylpyrazol-2-in-4-ol (A) to 3,5-diphenyl-1-methyl-4-pyrazolol (B) by standard procedures, are listed in Table II, wherein A and B are as above identified and C represents 3,5-diphenyl-1-methylpyrazole.

Table II

| Reagent | Reaction Conditions | Products Isolated |
|---|---|---|
| Chloranil | Δ, CH$_3$OH, 22.5 hrs. | C |
| 5% pd/C | Δ, CH$_3$CN, 22 hrs. | A, recovered |
| 5% Pd/C | Δ, xylene, 19 hrs. | C, + A, recovered |
| S | Δ, o-dichlorobenzene, 22 hrs. | C, + 15% B |
| S | Δ, xylene, 5 hrs | C, + 15% B |
| S | Δ, benzene, 66.5 hrs. melt, 10 minutes | C, + A, + unidentified material |
| S | Δ, DMF, 17 hrs. 110°C to 120°C | C |
| S | Δ, xylene/NaH, 17 hrs. | Trace of B, + unidentified products |
| MnO$_2$ | benzene, 21 hrs, 20°C | unidentified products |
| MnO$_2$-activated | benzene, 20 hrs, 20°C | unidentified products |
|  | Δ, CCl$_4$, 5 hrs. | C, + A, recovered |
|  | Δ, xylene, 17 hrs. | C, + A, recovered |
| I$_2$/NaHCO$_3$ | Δ, C$_2$H$_5$OH, 16 hrs. | unidentified products |
| HgO | Cold; Δ, benzene, 8 hrs. | C, + unidentified products |
| KMNO$_4$/NaOH | H$_2$O, 20°C | C, + A, + impurities |
| CrO$_3$ | pyridine | unidentified products |
| H$_2$O$_2$; and H$_2$O$_2$/I$_2$ | Δ, DMF, 100°C | unidentified products |
| Cu(OCOCH$_3$)$_2$ | Δ, CH$_3$OH, 2 hrs. | unidentified products |
| Pb(OCOCH$_3$)$_4$ | benzene, room temperature | 36% B |
| Pb(OCOCH$_3$)$_4$ | benzene, 10°C – 15°C | 36% B |
| Pb(OCOCH$_3$)$_4$ | pyridine | unidentified products |
| Pb(OCOCH$_3$)$_4$ | CH$_3$COOH | unidentified products |
| (NH$_4$)$_2$ Ce(NO$_3$)$_6$ | p-dioxane, 100°C | unidentified products |
| (NH$_4$)$_2$ Ce(NO$_3$)$_6$ · HCl | p-dioxane, 100°C | unidentified products |
| 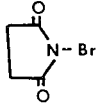 | Δ, CHCl$_3$, 3 hrs. | 36% B |

EXAMPLE 12

The postemergency herbicidal activity of 4-alkoxy- and benzyloxypyrazolium compounds, derived from the 3,5-diphenyl-4-pyrazolols of the present invention is demonstrated by the following tests, wherein a plurality of monocotyledonous and dicotyledonous plants is treated with test compounds dispersed in aqueous acetone mixtures. In the tests, seedling plants are grown in jiffy flats for about 2 weeks. The test compounds are dispersed in 50/50 acetone/water mixtures containing 0.5% TWEEN$^R$ 20, a polyoxyethylene sorbitain monolaurate surfactant, in sufficient quantity to provide the equivalent of about 0.5 lb to 10 lbs per acre of active compound when applied to the plants through a spray nozzle operating at 40 psi for a predetermined time. After spraying, the plants are placed on greenhouse benches and are cared for in the usual manner, commensurate with conventional greenhouse practices. Two weeks after treatment, the seedling plants are examined and rated according to the rating system provided below. The data obtained are reported in Table III, where it can be seen that the compounds are effective for the control of a variety of broadleaf weeds and grass weeds.

| Rating System: | % Difference in Growth from the Check* |
|---|---|
| 0 - No effect | 0 |
| 1 - Possible effect | 1 – 10 |
| 2 - Slight effect | 11 – 25 |
| 3 - Moderate effect | 26 – 40 |
| 5 - Definite injury | 41 – 60 |
| 6 - Herbicidal effect | 61 – 75 |
| 7 - Good herbicidal effect | 76 – 90 |
| 8 - Approaching complete kill | 91 – 99 |
| 9 - Complete kill | 100 |
| 4 - Abnormal growth; that is, a definite physiological malformation but with an over-all effect less than a 5 on the rating scale. | |

*Based on visual determination of stand, size, vigor, chlorosis, growth malformation and over-all plant appearance.

PLANT ABBREVIATIONS

SE — Sesbania (*Sesbania exaltata*)
LA — Lambsquarters (*Chenopodium album*)
MU — Mustard (*Brassica kaber*)
PI — Pigweed (*Amaranthus retroflexus*)
BA — Barnyardgrass (*Echinochloa crusgalli*)
CR — Crabgrass (*Digitaria sanguinalis*)
GRF — Green foxtail (*Setaria viridis*)
WO — Wild Oats (*Avena fatua*)
VL — Velvetleaf (*Abutilon theophrasti*)
TW — Teaweed (*Sida spinosa*)
RAG — Ragweed (*Ambrosia artemisiifolia*)
WH — Wheat (*Triticum vulgare*)
MG — Morningglory (*Ipomoca purpurea*)
BR — Barley (*Hordeum vulgare*)
RI — Rice (*Oryza sativa*)

Table III

Postemergence Herbicidal Activity of 4-Alkoxy and 4-Benzyloxypyrazolium Compounds, Derived from the 3,5-Diphenyl-4-pyrazolols of the Present Applications.

| Compounds | Treatment lb/acre | SE | LA | MU | PI | RAG | MG | BA | CR | GRF | WO | VL | TW | BR | RI | WH |
|---|---|---|---|---|---|---|---|---|---|---|---|---|---|---|---|---|
| 1,2-Dimethyl-3,5-diphenyl-4- | 4 | 8 | | 9 | | 9 | 8 | 5 | 2 | 8 | 9 | 8 | | 9 | | |

Table III-continued

Postemergence Herbicidal Activity of 4-Alkoxy and 4-Benzyloxypyrazolium Compounds, Derived from the 3,5-Diphenyl-4-pyrazolols of the Present Applications.

| Compounds | Treatment lb/acre | SE | LA | MU | PI | RAG | MG | BA | CR | GRF | WO | VL | TW | BR | RI | WH |
|---|---|---|---|---|---|---|---|---|---|---|---|---|---|---|---|---|
| methoxypyrazolium methyl | 1 | 3 | | | 9 | | 8 | 8 | 2 | 1 | 7 | 8 | 3 | | 7 | |
| sulfate | 0.5 | 2 | | | 3 | | 3 | 3 | 2 | 3 | 2 | 9 | 2 | | 9 | |
| 4-Benzyloxy-1,2-dimethyl-3,5- | 10 | 8 | | 9 | 9 | 0 | 6 | 3 | 2 | 3 | 2 | 9 | | | | |
| diphenylpyrazolium methyl | 3 | 8 | | 9 | 9 | 5 | 2 | 2 | 2 | 2 | 1 | 6 | | | | |
| sulfate | 1 | 0 | | 9 | 8 | 0 | 3 | 1 | 1 | 1 | 0 | | | | | |
| 1-Benzyl-3,5-diphenyl-4- | 10 | 8 | | 9 | 9 | 9 | 5 | 3 | 3 | 5 | 6 | 9 | 9 | | | |
| methoxy-2-methylpyrazolium | 4 | 9 | | 9 | 9 | 8 | 9 | 2 | 2 | 2 | 2 | 7 | 8 | | | |
| methyl sulfate | | | | | | | | | | | | | | | | |
| 1,2-Dimethyl-3,5-diphenyl-4-n- | 10 | 6 | | 9 | 9 | 9 | 1 | 5 | 3 | 6 | 7 | 6 | 9 | | | |
| propoxypyrazolium methyl | 4 | 9 | | 9 | 9 | 9 | 5 | 2 | 2 | 2 | 7 | 9 | 8 | 3 | | |
| sulfate . H₂O | 1 | 5 | | 9 | 9 | 0 | 5 | 1 | 1 | 1 | 2 | 6 | 7 | 1 | | |
| 1,2-Dimethyl-3,5-diphenyl-4-i- | 10 | 8 | | 9 | 9 | 6 | 5 | 3 | 5 | 1 | 3 | 8 | 7 | | | |
| propoxypyrazolium methyl | 4 | 9 | | 9 | 9 | 9 | 9 | 7 | 6 | 5 | | 8 | 6 | | 5 | |
| sulfate . H₂O | 1 | 3 | | 9 | 9 | 0 | 3 | 5 | 5 | 2 | | 2 | 2 | | 5 | |
| 3,5-Diphenyl-1-ethyl-4-methoxy- | 10 | 5 | | 9 | 9 | 7 | 9 | 8 | 1 | 2 | 5 | 9 | 9 | | | |
| 2-methylpyrazolium perchlorate | 4 | 7 | | | 8 | | 6 | | 1 | 1 | 0 | 2 | 8 | 1 | | |
| 3,5-Diphenyl-4-methoxy-2- | 10 | 7 | | 7 | 9 | 2 | 5 | 5 | 1 | 2 | 5 | 2 | 9 | | | |
| methyl-1-n-propylpyrazolium | 4 | 5 | | | 9 | | 1 | | 0 | 0 | 1 | 1 | 6 | | 5 | |
| perchlorate | | | | | | | | | | | | | | | | |

I claim:

1. A method for the preparation of a compound of the formula:

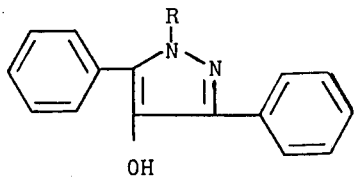

wherein R is selected from the group consisting of hydrogen and $C_1$–$C_6$ alkyl comprising the steps of: reacting a molar equivalent of a compound of the formula:

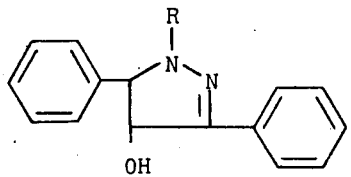

wherein R is as defined above, with a 1 to 1.2 molar equivalent of a compound of the formula:

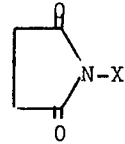

wherein X is bromine or chlorine, in the presence of an inert chlorinated hydrocarbon solvent at a temperature ranging between about 20° and 100°C, and recovering said 3,5-diphenylpyrazol-4-ol in good yield.

2. The method according to claim 1, wherein said compound is 3,5-diphenylpyrazol-4-ol.

3. The method according to claim 1, wherein said compound is 3,5-diphenyl-1-methylpyrazol-4-ol.

4. The method according to claim 1, wherein said compound is 3,5-diphenyl-1-ethylpyrazol-4-ol.

5. The method according to claim 1, wherein said compound is 3,5-diphenyl-1-n-propylpyrazol-4-ol.

6. The method according to claim 1, wherein the temperature range is between 20° to 60°C.

7. The method according to claim 1, wherein said solvent is chloroform.

* * * * *